(12) United States Patent
Moriyasu

(10) Patent No.: US 8,913,711 B2
(45) Date of Patent: Dec. 16, 2014

(54) PHOTON COUNTING TYPE X-RAY COMPUTED TOMOGRAPHY APPARATUS AND METHOD FOR CORRECTING SCATTERED RADIATION

(71) Applicants: Kabushiki Kaisha Toshiba, Minato-Ku (JP); Toshiba Medical Systems Corporation, Otawara (JP)

(72) Inventor: Kenta Moriyasu, Nasushiobara (JP)

(73) Assignees: Kabushiki Kaisha Toshiba, Minato-Ku (JP); Toshiba Medical Systems Corporation, Otawara-shi (JP)

( * ) Notice: Subject to any disclaimer, the term of this patent is extended or adjusted under 35 U.S.C. 154(b) by 82 days.

(21) Appl. No.: 13/856,681

(22) Filed: Apr. 4, 2013

(65) Prior Publication Data

US 2013/0223587 A1 Aug. 29, 2013

Related U.S. Application Data

(63) Continuation of application No. PCT/JP2012/070833, filed on Aug. 16, 2012.

(30) Foreign Application Priority Data

Aug. 18, 2011 (JP) ................................ 2011-178943

(51) Int. Cl.
*G01N 23/04* (2006.01)
*A61B 6/00* (2006.01)
*A61B 6/03* (2006.01)

(52) U.S. Cl.
CPC .................. *A61B 6/032* (2013.01); *A61B 6/482* (2013.01); *A61B 6/03* (2013.01); *A61B 6/5235* (2013.01)
USPC .................................................. 378/7; 378/4

(58) Field of Classification Search
USPC .............................................. 378/4, 7, 16, 20
See application file for complete search history.

(56) References Cited

U.S. PATENT DOCUMENTS

| 6,754,298 B2 * | 6/2004 | Fessler .............................. 378/4 |
| 8,041,096 B2 | 10/2011 | Bernhardt et al. |
| 2006/0175552 A1 | 8/2006 | Kojima et al. |
| 2008/0226019 A1 * | 9/2008 | Thran et al. ....................... 378/7 |

FOREIGN PATENT DOCUMENTS

| JP | 2006-101926 | 4/2006 |
| JP | 2006-214916 | 8/2006 |
| JP | 2008-272476 | 11/2008 |

OTHER PUBLICATIONS

International Preliminary Report on Patentability and Written Opinion issued Feb. 18, 2014 in PCT/JP2012/070833 (submitting English translation only).
International Search Report issued on Nov. 13, 2012 for PCT/JP2012/070833 filed on Aug. 16, 2012 with English Translation.

* cited by examiner

*Primary Examiner* — Hoon Song
(74) *Attorney, Agent, or Firm* — Oblon, Spivak, McClelland, Maier & Neustadt, L.L.P.

(57) ABSTRACT

A CT apparatus includes: a tube that produces an X-ray photon whose highest energy is higher than highest peak energy of characteristic X-rays; a detecting material; a unit that produces a first attenuation coefficient map which corresponds to a first energy region including the highest peak energy of the characteristic X-rays; a unit that transforms the first attenuation coefficient map into a second attenuation coefficient map of a second energy region; a unit that produces a scattered photon distribution of scattered X-ray photons on the basis of the second attenuation coefficient map; and a unit that produces data before reconstruction on the basis of the detected X-ray photon which corresponds to the second energy region, corrects and processes the data before reconstruction with the scattered photon distribution so as to produce corrected data, and reconstructs an image corresponding to the second energy region for which scattered radiation is corrected.

12 Claims, 9 Drawing Sheets

PHOTON COUNTING TYPE X-RAY COMPUTED TOMOGRAPHY APPARATUS AND METHOD FOR CORRECTING SCATTERED RADIATION

CROSS-REFERENCE TO RELATED APPLICATION

This application is a Continuation Application of No. PCT/JP2012/070833, filed on Aug. 16, 2012, and the PCT application is based upon and claims the benefit of priority from Japanese Patent Application No. 2011-178943, filed on Aug. 18, 2011, the entire contents of which are incorporated herein by reference.

FIELD

An embodiment of the invention relates to a photon counting type X-ray computed tomography apparatus (X-ray CT apparatus) which counts X-ray photons (particles) and a method for correcting scattered radiation.

BACKGROUND

An X-ray CT apparatus has an X-ray tube and an X-ray detector arranged opposite each other on both sides of a test object. The X-ray detector has a plurality of channels of detecting elements along a direction perpendicular to a longer side direction of a table-top (channel direction) being a direction of a body axis of the test object.

Various types of X-ray detectors can be used for the X-ray CT apparatus. One of detectors being used for the X-ray CT apparatus in general is a scintillation detector. Elements in the scintillation detector each have a scintillator and an optical sensor such as a photodiode (PD). Further, a photon counting type X-ray CT apparatus which uses a semiconductor detector fit for photo-counting is being studied in recent years. The semiconductor detector has a semiconductor cell (X-ray detecting material) and a plurality of processing circuits formed by an ASIC layer in general.

The X-ray CT apparatus being used at present in general does not read information on detected X-ray energy, though, and is thus unable to quantitatively correct scattered radiation.

In addition, X-rays produced by the x-ray tube has energy in a broad spectrum. Thus, even if a photon counting type detector which reads information on X-ray energy is used, it cannot be distinguished whether the detected X-rays are of scattered radiation or X-rays having passed through the test object without any reaction, and no quantitative method for correcting scattered radiation has been established yet.

BRIEF DESCRIPTION OF THE DRAWINGS

In accompanying drawings.

DETAILED DESCRIPTION

Figure 1:
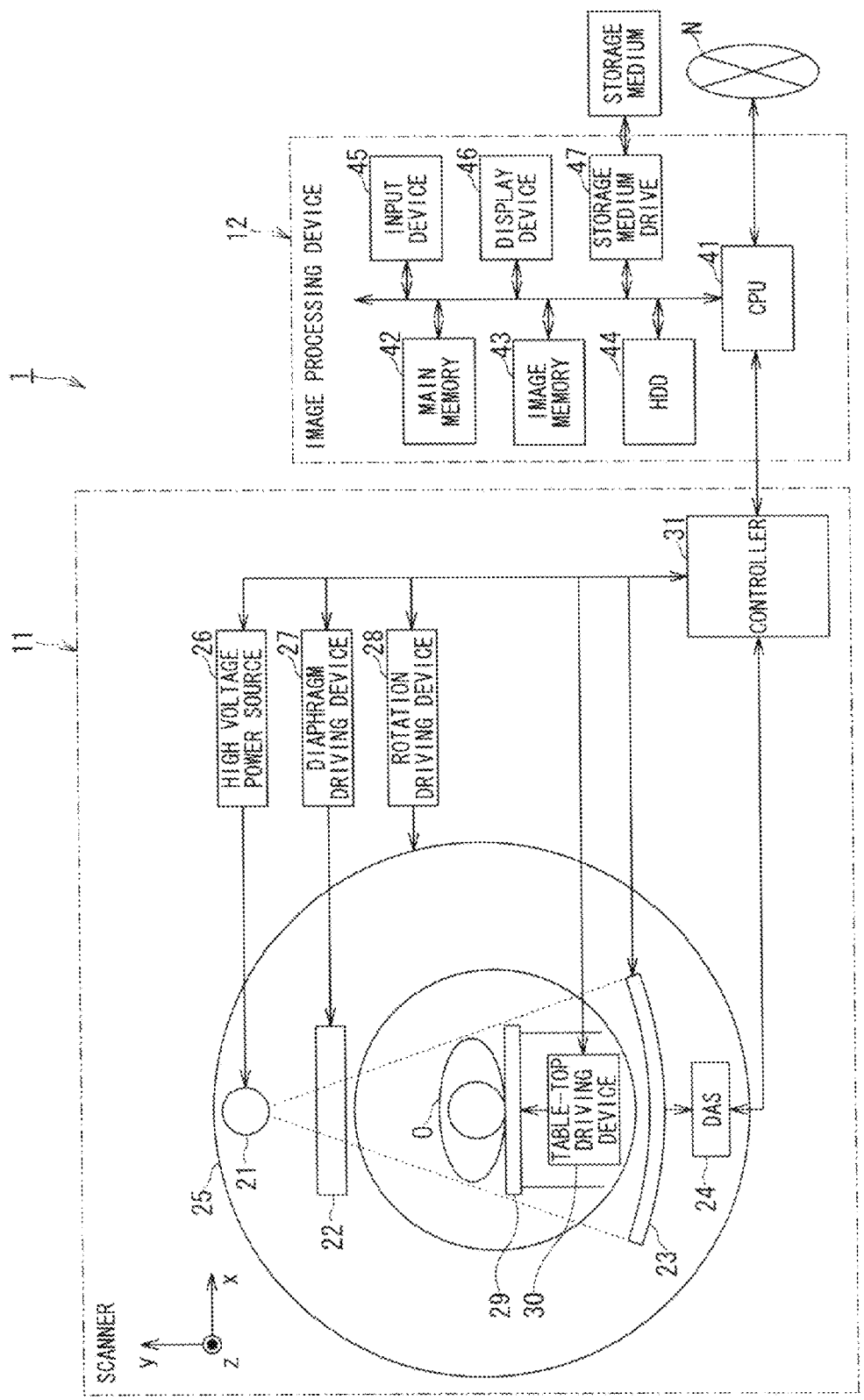
FIG. 1 is a hardware configuration diagram showing a photon counting type X-ray CT apparatus according to a present embodiment.

An X-ray CT apparatus and a method for correcting scattered radiation of the embodiment will be explained with reference to the drawings.

To solve the above-described problems, the present embodiments provide the photon counting type X-ray CT apparatus including: an X-ray tube configured to produce an X-ray photon whose highest energy is higher than highest peak energy of characteristic X-rays; an X-ray detecting material configured to detect the X-ray photon; an attenuation coefficient map producing unit configured to produce a first attenuation coefficient map which corresponds to a first energy region including the highest peak energy of the characteristic X-rays; an attenuation coefficient map transforming unit configured to transform the first attenuation coefficient map into a second attenuation coefficient map of a second energy region which is different from the first energy region; a simulation performing unit configured to perform a simulation of scattered radiation on the basis of the second attenuation coefficient map so as to produce a scattered photon distribution of scattered X-ray photons; and an image reconstructing unit configured to produce data before reconstruction on the basis of the detected X-ray photon which corresponds to the second energy region, to correct and process the data before reconstruction with the scattered photon distribution so as to produce corrected data, and to reconstruct an image corresponding to the second energy region for which scattered radiation is corrected.

To solve the above-described problems, the present embodiments provide the method for correcting scattered radiation including: producing an X-ray photon whose highest energy is higher than highest peak energy of characteristic X-rays from an X-ray tube; detecting the X-ray photon by means of an X-ray detecting material; producing a first attenuation coefficient map which corresponds to a first energy region including the highest peak energy of the characteristic X-rays; transforming the first attenuation coefficient map into a second attenuation coefficient map of a second energy region which is different from the first energy region; performing a simulation of scattered radiation on the basis of the second attenuation coefficient map so as to produce a scattered photon distribution of scattered X-ray photons; and producing data before reconstruction on the basis of the detected X-ray photon which corresponds to the second energy region, correcting and processing the data before reconstruction with the scattered photon distribution so as to produce corrected data, and reconstructing an image corresponding to the second energy region for which scattered radiation is corrected.

There are various types of X-ray CT apparatuses of the present embodiment, such as a ROTATE/ROTATE type in which an X-ray tube and an X-ray detector rotate as one body around an object, a STATIONARY/ROTATE type in which a large number of detection elements are arrayed in a ring-shape, and only the X-ray tube rotates around the object, and the like. The present invention can be applied to any of those types. Hereafter, the ROTATE/ROTATE type which is currently in a mainstream position will be described.

Further, the current mainstream of the mechanism for converting incoming X-ray into electric charge includes an indirect conversion type in which X-ray is converted into light with a fluorescent body such as a scintillator, etc., and the light is converted into electric charge with a photoelectric conversion element such as a photodiode, etc., and a direct conversion type in which the generation of an electron-hole pair in a semiconductor and the transfer thereof to an electrode, that is, a photoconductive phenomenon is utilized.

In addition, in recent years, a progress has been made in the commercialization of a so-called multi-tube type X-ray CT apparatus, in which a plurality of pairs of the X-ray tube and the X-ray detector are mounted on a rotary ring, and the development of peripheral technologies thereof has been in progress. The X-ray CT apparatus of the present embodiment can be applied to either of a conventional single-tube type X-ray CT apparatus, or a multi-tube type X-ray CT apparatus. Here, description will be made supposing a single-tube type X-ray CT apparatus.

FIG. 1 is a hardware configuration diagram showing a photon counting type X-ray CT apparatus according to the embodiment.

FIG. 1 shows a photon counting type X-ray CT apparatus 1 according to the present embodiment. The X-ray CT apparatus 1 is broadly formed by a scanner 11 and an image processing device 12. The scanner 11 of the X-ray CT apparatus 1 is ordinarily installed in a test room, and is configured to produce X-ray pass-through data regarding the part of a patient (test object) O. Meanwhile, the image processing device 12 is ordinarily installed in a control room next to the test room, and is configured to produce projection data on the basis of the pass-through data so as to produce and display a reconstructed image.

The scanner 11 of the X-ray CT apparatus 1 is provided with an X-ray tube 21, a diaphragm 22, a photon counting type image detector (simply called "detector" hereafter) 23, a DAS (data acquisition system) 24, a rotation section 25, a high voltage power source 26, a diaphragm driving device 27, a rotation driving device 28, a table-top 29, a table-top driving device 30 and a controller 31.

The X-ray tube 21 hits a metallic target made of tungsten (W), etc., with an electron beam in accordance with a tube voltage supplied by the high voltage power source 26 so as to produce X-rays, and radiates the X-rays toward the detector 23. The X-rays radiated by the X-ray tube 21 form fan beam X rays or cone beam X-rays. The X-ray tube 21 is supplied with power needed for X-ray radiation as controlled by the controller 31 via the high voltage power source 26.

The diaphragm 22 adjusts ranges in a slice direction and in a direction perpendicular thereto to be irradiated with the X-rays radiated by the X-ray tube 21 by means of the diaphragm driving device 27. That is, the diaphragm driving device 27 adjusts an aperture of the diaphragm 22, so that the ranges in the slice direction and in the direction perpendicular thereto to be irradiated with the X-rays can be changed.

The detector 23 has a plurality of channels and a plurality of columns of pixels in channel and slice directions, respectively, in a matrix form. In addition, the detector 23 has curvature in the channel direction as an angle at which the X-ray beams spread out from the X-ray tube 21 is taken into account. Incidentally, the entire shape of the detector 23 is determined according to its use, and may be like a flat plate. Although a semiconductor detector will be exemplarily explained hereafter, the invention can be applied not only to the semiconductor detector but to any detector which enables a photon counting operation.

Figure 2:
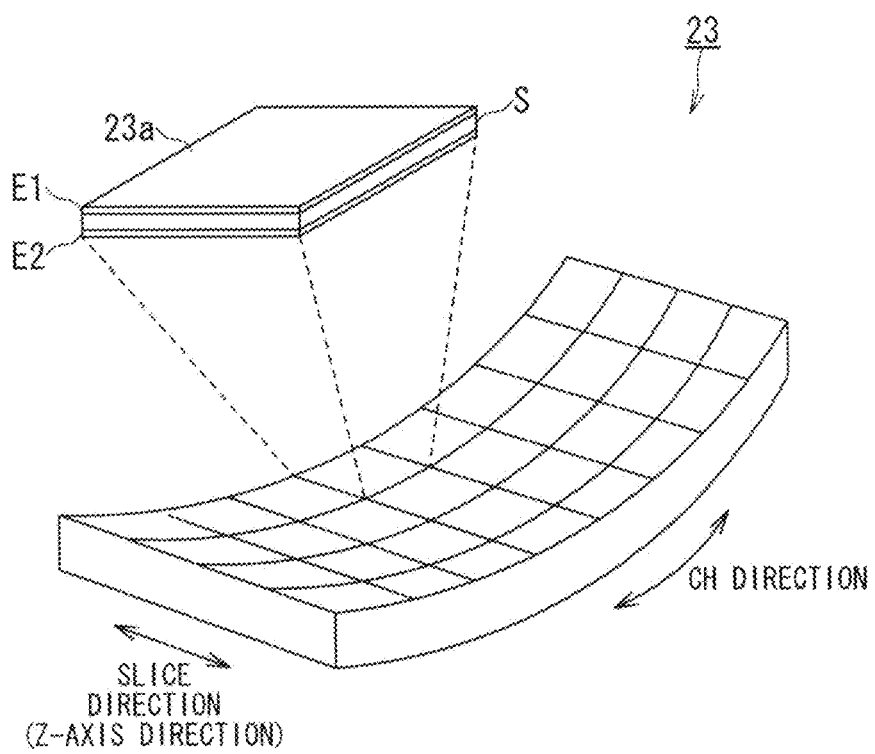
FIG. 2 is a diagrammatic perspective view for explaining a structure of a photon counting type image detector.

FIG. 2 is a diagrammatic perspective view for explaining a structure of the detector.

As shown in FIG. 2, the detector 23 is divided into a plurality of detector blocks 23a in such a way that a 2D face is divided into a plurality of sub-faces, and the plural detector blocks 23a can be coupled with and separated from one another. Further, the detector 23 is configured to obtain an X-ray see-through image from the X-ray tube 21 in condition that a collimator made of molybdenum or tungsten which is not shown is arranged in the slice direction in front of an X-ray incidence side of the detector blocks 23a.

The detector blocks 23a each have a monolithic structure in which a semiconductor cell S formed by a compound semiconductor in layers in a particular size (e.g., several centimeters times several centimeters) is covered on the radiation incidence face by a charged electrode E1 for voltage application and on a back face of the radiation incidence face by a plurality of collecting electrodes E2 into which the back face is divided in 2D arrays (checkerboard squares). The collecting electrodes E2 each correspond to respective pixels. Materials such as a cadmium telluride semiconductor (CdTe semiconductor), a cadmium zinc telluride semiconductor (CdZnTe semiconductor), a silicon semiconductor (Si semiconductor), etc., are used for the semiconductor cell S. A relatively high voltage, e.g., several dozens to several hundred volts is applied to the charged electrode E1. An X-ray photon having arrived at the semiconductor cell S thereby produces an electron-hole pair inside, and the electron is collected by each of the collecting electrodes E2 given a relatively positive voltage, so that an electric charge carried by the electron is detected as a pulse-like signal. That is, the X-rays having met the radiation incidence face are directly converted into a pulse signal of an electric quantity.

The pixel size for X-rays is determined by the size of each of the plural collective electrodes E2 separated from one another like checkerboard squares. The pixel size is small enough to detect X-rays on a photon (particle) basis. The detector 23 which enables a photon counting operation is thereby structured, and matrix like pixel channels as many as a particular number are formed in the entire detector 23.

The X-rays having passed through the patient O are counted by the detector 23 as X-ray particles (i.e., X-ray photons) every fixed period of time, and a detected signal is outputted by every pixel P (pixels P1-Pk) in an analog quantity according to photon energy.

The detected signals of the respective pixels outputted by the detector 23 are sent to the data acquisition system (DAS) 24.

Figure 3:
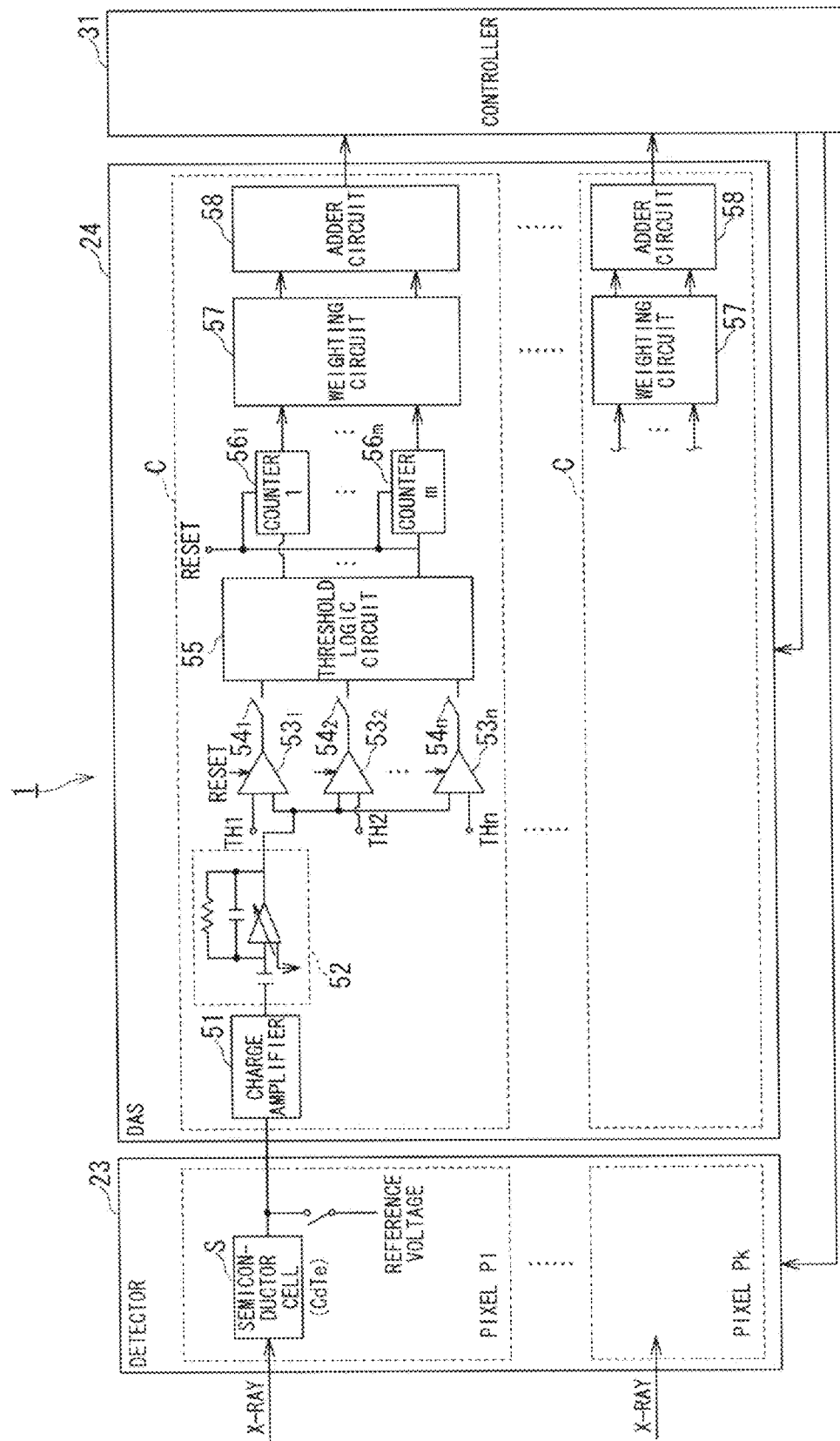
FIG. 3 is an electric block diagram centered on the photon counting type image detector and a DAS.

FIG. 3 is an electric block diagram centered on the detector 23 and the DAS 24.

As shown in FIG. 3, the detector 23 has the semiconductor cell S to be controlled by the controller 31 in each of the pixels P.

The DAS 24 has a processing circuit C to be controlled by the controller 31 for each of the pixels P. The processing circuit C has a charge amplifier 51, a waveform shaping circuit 52, comparators (Dual Discri) of n stages (n is a positive integer) $53_1$-$53_n$, switches of n stages $54_1$-$54_n$, a threshold logic circuit (Discri Logic) 55, counters (Counter CLK) of m stages (m is a positive integer) $56_1$-$56_m$, a weighting circuit 57 and an adder circuit 58.

The charge amplifier 51 is coupled with each of the plural collecting electrodes E2 of the semiconductor cell S. The charge amplifier 51 outputs electric charges collected in response to incidence of an X-ray particle as a voltage pulse signal. An output end of the charge amplifier 51 is coupled with the waveform shaping circuit 52 whose gain and offset can be adjusted.

The waveform shaping circuit 52 processes a waveform of a detected voltage pulse signal according to a gain and an offset adjusted beforehand for waveform shaping. The gain and the offset of the waveform shaping circuit 52 are adjustment parameters for which unevenness of charge-up characteristics for electric charges of each of the pixels in the semiconductor cell S is taken into account. If the gain and the offset of the waveform shaping circuit 52 is adjusted beforehand for every pixel through calibration work, waveform shaping having excluded such unevenness can be done. As a result, a waveform-shaped pulse signal outputted by the waveform shaping circuit 52 of each of collection channels has a characteristic on which an amount of energy of the incident X-ray particle is substantially reflected, and such unevenness among the pixels is substantially solved. An output end of the waveform shaping circuit 52 is coupled with a compared input end of each of the plural comparators $53_1$-$53_n$.

Reference values TH1 (upper limit reference value THH) through THn (lower limit reference value THL) which are different from one another are each applied to reference input ends of the comparators $53_1$-$53_n$, respectively. A peak value of one pulse signal (energy of an absorbed X-ray photon) coming from the waveform shaping circuit 52 is compared with the reference values TH1-THn which are different from one another so that the energy of the X-ray photon (X-ray particle) absorbed by the semiconductor cell S can be classified into one of plural energy regions which are separated and set beforehand. If n equals three, e.g., the energy region into which the X-ray energy is classified differs depending upon which of the reference values TH1-TH3 the peak value of the pulse signal is over. If the peak value is between the reference values TH1 and TH2, the energy of the absorbed X-ray photon is classified as being included in a first energy region. If the peak value is between the reference values TH2 and TH3, the energy of the absorbed X-ray photon is classified as being included in a second energy region. If the peak value is equal to or lower than the reference value TH3 (lower limit reference value THL) or equal to or higher than the reference value TH1 (upper limit reference value THH), the X-ray energy is classified in such a way that a disturbance or white noise coming from the semiconductor cell S or the charge amplifier 51 is prevented from being detected. The case where the peak value is equal to or higher than the reference value TH1 (upper limit reference value THH) may occur as well if two or more X-ray photons arrive at the pixel at the same time. Such an event is considered to improbably occur here, though, and is treated as not relating to a main signal forming image information similarly as a disturbance.

Incidentally, the number of the reference values, i.e., the number of the energy regions which are distinguishable from one another is not limited to three. The number of the reference values may be two, four, etc., or may be one depending upon circumstances. If the number of the reference values is one, information on only whether an X-ray photon has arrived is obtained. The output ends of the comparators $53_1$-$53_n$ are coupled with the switches $54_1$-$54_n$, respectively.

The switches $54_1$-$54_n$ are designed to be each turned on if a pulse signal outputted from a corresponding one of the comparators $53_1$-$53_n$ is over a corresponding one of the reference values TH1-THn of the switches $54_1$-$54_n$, respectively, and to be each turned off otherwise. The switch $54_1$, e.g., is designed to be turned on if a pulse signal outputted from the comparator $53_1$ is over the reference value TH1 of the switch $54_1$, and to be turned off otherwise. The output ends of the switches $54_1$-$54_n$ are each coupled with the threshold logic circuit 55.

The threshold logic circuit 55 checks which of the comparators $53_1$-$53_n$ are on (off) on the basis of pulse signals outputted individually by the switches $54_1$-$54_n$, and produces a clock pulse signal so as to count output pulses corresponding to a largest pulse signal of one of the comparators $53_1$-$53_n$ being on. Plural output ends of the threshold logic circuit 55 are individually coupled with each of plural counters $56_1$-$56_m$ so that the clock pulses are counted. The plural counters $56_1$-$56_m$ each work in such a way as to count correspondingly to the peak value of the pulse signal. A pulse being over TH2 and smaller than TH1, e.g., is counted by the counter $56_1$, and a pulse being over TH3 and smaller than TH2 is counted by the counter $56_2$ (similarly hereinafter). In this case, the number m of necessary counters is written as m=n−1 by the use of the number n of the comparators.

The number m of the counters is sometimes m<n−1, as another example, by the use of the number n of the comparators. That corresponds to a case where the number of the pulses having been peak-distinguished by the respective comparators is counted not in each of peak value ranges but in ranges each formed by gathered plural peak value ranges. The smallest number m of the counters is m=1. As the clock pulses outputted by the threshold logic circuit 55 is counted by one counter in this case, the counter counts the number of photons without distinguishing the energy of the X-ray photons.

The counters $56_1$-$56_m$ each count the clock pulses outputted by the threshold logic circuit 55 up and measure the number of X-ray photons being in the energy region that the relevant counter is in charge of for a certain period of time.

The weighting circuit 57 weights counted values outputted individually by the counters $56_1$-$56_m$.

The adder circuit 58 adds weighted counted values in each of the energy regions outputted by the weighting circuit 57 to one another, so as to produce raw data (data before reconstruction) for every pixel P, and sends the raw data to the image processing device 12 via the controller 31.

As described above, the DAS 24 counts the number of the X-ray photons having arrived at the respective pixels P of the detector 23 by means of the plural counters $56_1$-$56_m$ in each of the energy regions which correspond to the number m of the stages of the counters for a certain period of time until being reset. Resultant counted values, i.e., counted numbers of the X-ray photons are read from the plural counters $56_1$-$56_m$ as detected data (raw data) in digital quantities. The data is read for every pixel P in the ASIC layer AS.

Return to explanation in FIG. 1. The rotation section 25 holds the X-ray tube 21, the diaphragm 22, the detector 23 and the DAS 24 as one. The rotation section 25 is configured to rotate the X-ray tube 21, the diaphragm 22, the detector 23 and the DAS 24 around the patient O as one in condition that the X-ray tube 21 is put opposite the detector 23. Incidentally, a direction parallel to a central axis of rotation of the rotation section 25 is defined as a z-axis direction, and a plane perpendicular to the z-axis direction is defined as including x-axis and y-axis directions.

The high voltage power source 26 supplies the X-ray tube 21 with power necessary for X-ray radiation as controlled by the controller 31.

The diaphragm driving device 27 has a mechanism to adjust radiation ranges in the slice direction and in the direction perpendicular thereto to be irradiated with the X-rays on the diaphragm 22 as controlled by the controller 31.

The rotation driving device 28 has a mechanism to rotate the rotation section 25 as controlled by the controller 31 so that the rotation section 25 rotates around a cavity portion while maintaining its relative position.

The table-top 29 is a portion on which the patient O can be laid.

The table-top driving device 30 has a mechanism to move the table-top 29 up and down along the y-axis direction and inwards and outwards along the z-axis direction as controlled by the controller 31. The rotation section 25 has an aperture in its middle portion and the patient O laid on the table-top 29 is carried into the aperture.

The controller 31 is formed by a CPU (central processing unit) and a memory. The controller 31 controls the detector 23, the DAS 24, the high voltage power source 26, the diaphragm driving device 27, the rotation driving device 28, the table-top driving device 30, etc., and makes them carry out a scan.

The image processing device 12 of the photon counting type X-ray CT apparatus 1 has a computer-based structure and can interactively communicate with a network N such as an in-hospital backbone LAN (local area network). The image processing device 12 is broadly formed by basic hardware components such as a CPU 41, a main memory 42, an image memory 43, an HDD (hard disc drive) 44, an input device 45, a display device 46, etc. The CPU 41 is mutually coupled with the respective hardware components which form the image processing device 12 via a bus being a common signal transmission path. Incidentally, the image processing device 12 may sometimes have a storage medium drive 47.

The CPU 41 is a control device having a structure of an integrated circuit (LSI) in which an electronic circuit formed by a semiconductor is enclosed in a package having plural terminals. Upon being provided with instructions according to operation, etc., of the input device 45 performed by an operator such as a medical doctor, the CPU 41 runs a program stored in the main memory 42. Otherwise, the CPU 41 loads the main memory 42 with a program stored in the HDD 44, a program transferred from the network N and installed in the HDD 44 or a program read from a storage medium inserted into the storage medium drive 47 and installed in the HDD 44, and runs the program.

The main memory 42 is a storage including a ROM (read only memory), a RAM (random access memory), etc. The main memory 42 stores an IPL (initial program loader), a BIOS (basic input/output system) and data, and is used as a work memory for the CPU 41 or temporary storage of data.

The image memory 43 is a storage device which stores produced raw data and reconstructed image data.

The HDD 44 is a storage device having a structure in which a metallic disk not being removable that magnetic substance is applied to or laid on by vapor deposition is contained. The HDD 44 is a storage device in which a program (including an OS (operating system), etc., as well as an application program) or data is stored. Further, it is practical to make the OS provide a GUI (graphical user interface) in which graphics are used a lot for presenting information to the operator and basic operations can be done by means of the input device 45.

The input device 45 is a pointing device that the operator can operate, and an input signal according to an operation is sent to the CPU 41.

The display device 46 includes an image composing circuit, a VRAM (video random access memory), a display monitor, etc., which are not shown. The image composing circuit combines image data with text data of various parameters, etc. so as to produce composed data. The VRAM unfolds the composed data as display image data to be displayed on the display monitor. The display monitor is formed by an LCD monitor, a CRT (cathode ray tube), etc., and displays the display image data as displayed images in turn.

The storage medium drive 47 configured to be loaded with a removable storage medium reads data (including a program) stored in the storage medium so as to output the read data onto the bus, and writes data provided via the bus into the storage medium. So called package software can be provided as being stored in such a storage medium.

The image processing device 12 performs a logarithmic transformation process and a correction process (preprocess) for correcting sensitivity, etc., on the raw data provided by the DAS 24 of the scanner 11 via the controller 31 so as to produce projection data (data before reconstruction). Further, the image processing device 12 performs a process for removing scattered radiation on the preprocessed projection data.

Figure 4:
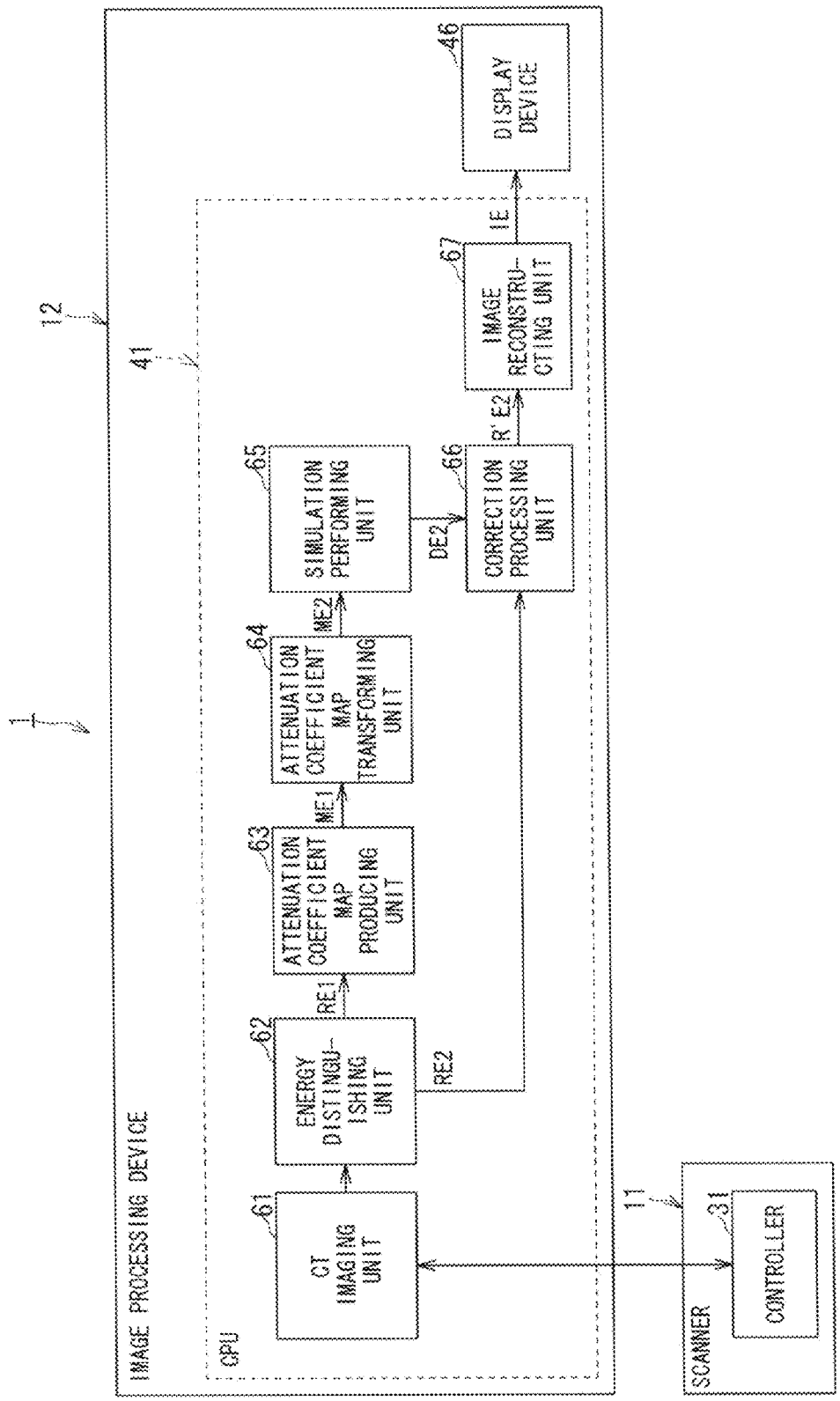
FIG. 4 is a block diagram showing a function of the photon counting type X-ray CT apparatus according to the present embodiment.

FIG. 4 is a block diagram showing a function of the photon counting type X-ray CT apparatus 1 according to the present embodiment.

The CPU 41 (or the controller 31) shown in FIG. 1 runs a program so that the X-ray CT apparatus 1 works as a CT imaging unit 61, an energy distinguishing unit 62, an attenuation coefficient map producing unit 63, an attenuation coefficient map transforming unit 64, a simulation performing unit 65, a correction processing unit 66 or an image reconstructing unit 67. Incidentally, the X-ray CT apparatus 1 may be equipped with all or part of the respective units 61-67 in hardware forms.

The CT imaging unit 61 has a function to control operation of the scanner 11 via the controller 31 so as to image an imaging part of the patient O. Think of X-ray photons detected by a certain pixel of the detector 23 here. A ratio of X-ray photons of highest peak energy (energy of Kα rays) of characteristic X-rays caused by reduction of energy of scattered ray photons scattered by the patient O to X-ray photons of highest peak energy (energy of Kα rays) having passed through the patient O without any reaction is considered to be negligibly small. Thus, the CT imaging unit 61 will do upon controlling a tube voltage on the X-ray tube 21 via the controller 31 so as to make the highest energy of the X-ray photons produced by the X-ray tube 21 higher than the highest peak energy of the characteristic X-rays.

Further, the CT imaging unit 61 may be configured to be affected by the X-ray photons of the highest peak energy (energy of Kα rays) of the characteristic X-rays caused by the reduction of energy of the scattered ray photons scattered by the patient O as little as possible, i.e., to make the number of such X-ray photons infinitesimally close to zero. In that case, the CT imaging unit 61 controls the tube voltage on the X-ray tube 21 via the controller 31 so as to make the highest energy of the X-ray photons produced by the X-ray tube 21 substantially equal the highest peak energy of the characteristic X-rays. If tungsten is selected as target material of the X-ray tube 21, the CT imaging unit 61 controls the tube voltage on the X-ray tube 21 via the controller 31 so as to make the highest energy of the X-ray photons close to the highest peak energy of the characteristic X-rays and higher than the highest peak energy, in order to avoid reduction of energy of scattered ray photons resulting in the highest peak energy (around 60 keV) of characteristic X-rays produced by the tungsten as much as possible. Incidentally, it goes without saying that the highest peak energy of the characteristic X-rays is changed if the target of the X-ray tube 21 is changed.

A case where the CT imaging unit 61 controls the tube voltage on the X-ray tube 21 via the controller 31 so as to make the highest energy of the X-ray photons produced by the X-ray tube 21 substantially equal the highest peak energy of the characteristic X-rays will be explained below.

Figure 5:
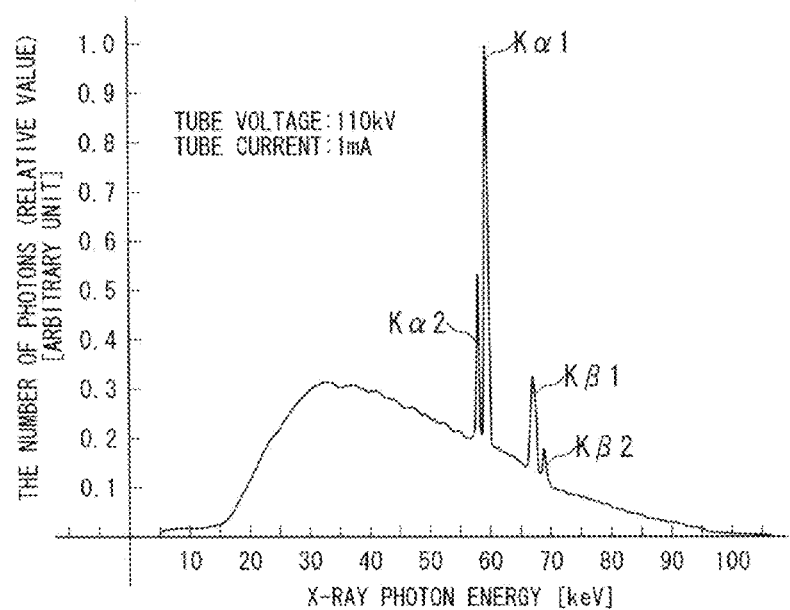
FIG. 5 is an exemplary energy spectrum of X-ray photons produced by X-ray tube.

FIG. 5 is an exemplary energy spectrum of X-ray photons produced by the X-ray tube 21.

FIG. 5 shows an energy spectrum of X-ray photons produced by the X-ray tube 21 for which tungsten is selected as the target at a tube voltage 110 kV and a tube current 1 mA. The X-ray photons produced by the X-ray tube 21 have an energy width. Further, the energy spectrum includes energy peaks of the characteristic X-rays (K$\alpha$1, K$\alpha$2, K$\beta$1 and K$\beta$2 rays) called K-absorption edges.

Figure 6:
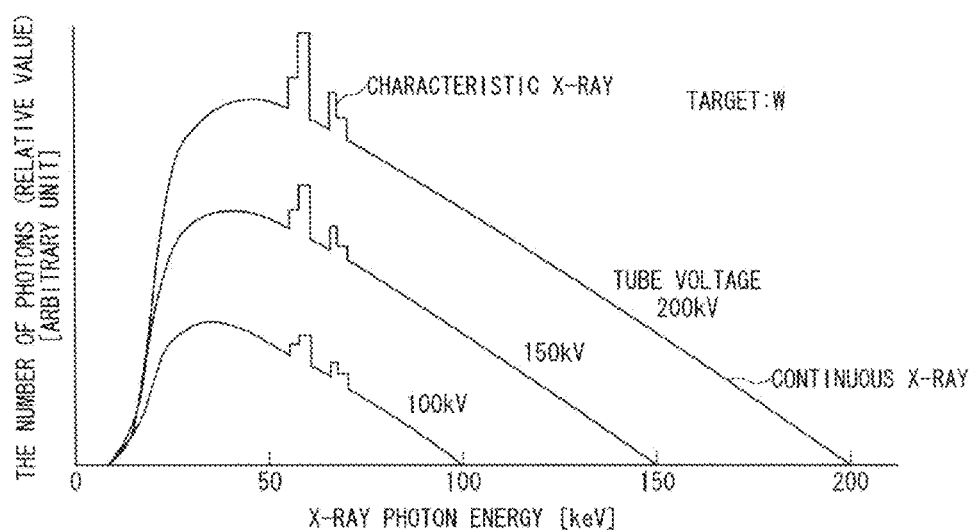
FIG. 6 is a change in energy spectrum of X-ray photons in a case where the tube voltage is changed.

FIG. 6 is a change in energy spectrum of X-ray photons in a case where the tube voltage is changed.

In the energy spectrum of the X-ray photons shown in FIG. 6, a filter is added so that soft rays (low energy component) are removed. Although a line width of characteristic X-rays is very narrow by nature, a certain width is given in FIG. 6 for easier viewing. Meanwhile, continuous X-rays span a broad spectrum.

If the tube voltage on the X-ray tube 21 decreases as controlled by the CT imaging unit 61, the highest energy of the X-ray photons produced by the X-ray tube 21 decreases as shown in FIG. 6.

Figure 7:
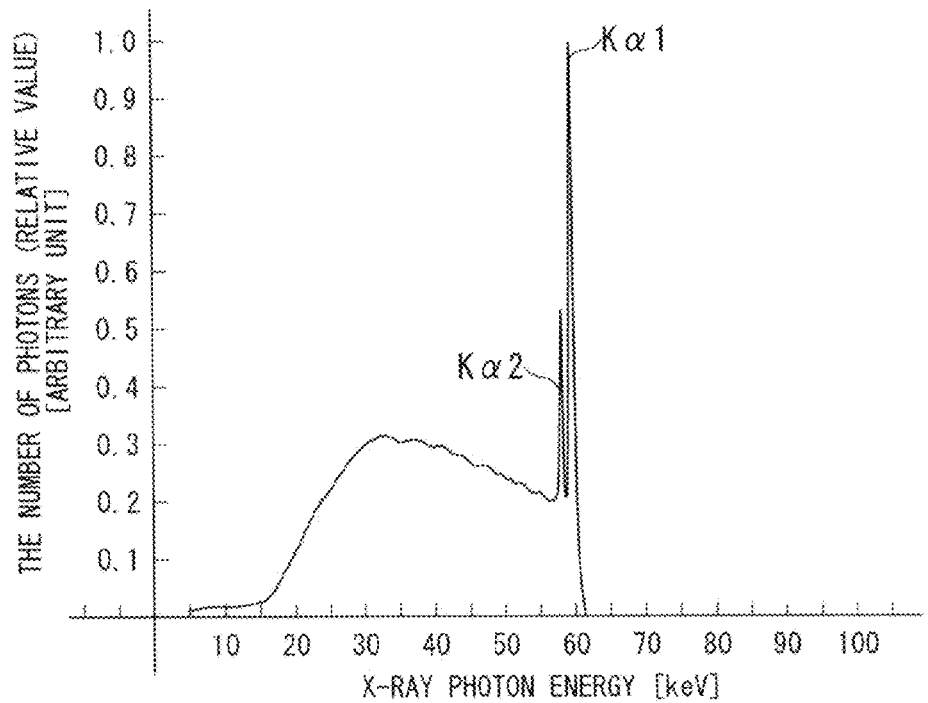
FIG. 7 is an exemplary energy spectrum of X-ray photons whose highest energy is controlled.

FIG. 7 is an exemplary energy spectrum of X-ray photons whose highest energy is controlled.

The CT imaging unit 61 controls the tube voltage on the X-ray tube 21 so as to make the highest energy of the X-ray photons close to the highest peak energy and higher than the highest peak energy as shown in FIG. 7.

The energy distinguishing unit 62 shown in FIG. 4 has a function to control operation of the DAS 24 via the controller 31 so as to distinguish raw data (data before reconstruction) RE1 in an energy region E1 including the highest peak energy of the characteristic X-rays and to distinguish raw data RE2 in one or a plurality of energy regions E2 which are different from (lower than) the energy region E1. A case where the energy distinguishing unit 62 distinguishes raw data of 60 keV as the raw data RE1 in the energy region E1 will be explained below.

The attenuation coefficient map producing unit 63 has a function to reconstruct a reconstructed image on the basis of the raw data RE1 in the energy region E1 distinguished by the energy distinguishing unit 62 so as to produce the reconstructed image, i.e., to produce an attenuation coefficient map ME1 on the basis of the raw data RE1 in the energy region E1 distinguished by the energy distinguishing unit 62. The attenuation coefficient map ME1 produced by the attenuation coefficient map producing unit 63 is what is hardly affected by scattered X-ray photons.

Figure 8:
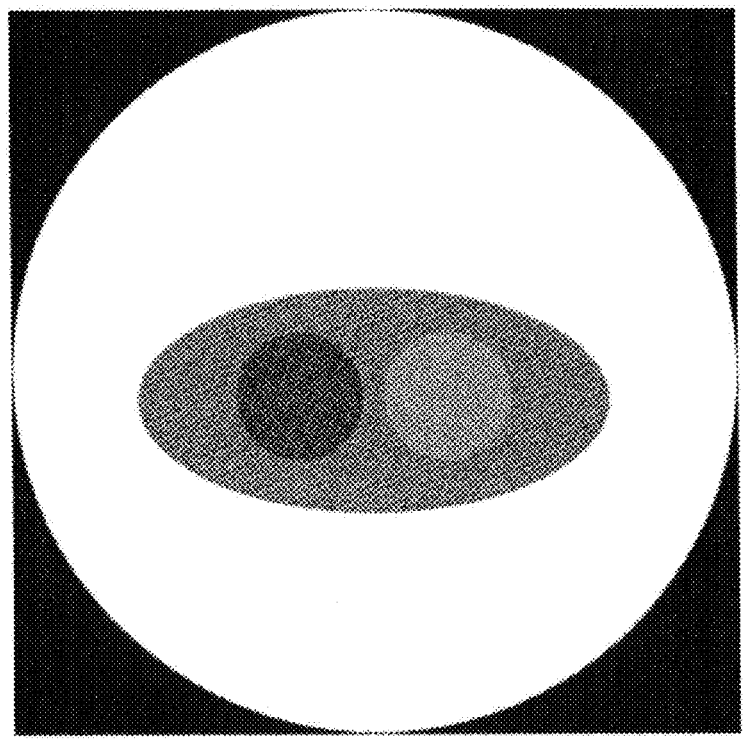
FIG. 8 is an example of an attenuation coefficient map based on raw data in an energy region including the highest peak energy of characteristic X-rays.

FIG. 8 is an example of the attenuation coefficient map ME1 based on the raw data RE1 in the energy region E1 including the highest peak energy of the characteristic X-rays.

FIG. 8 shows the attenuation coefficient map ME1 obtained after image reconstruction is done by the use of the raw data RE1 in the energy region E1 only. If the output of the X-ray tube 21 is adjusted so that X-rays having energy higher than the highest peak energy of the characteristic X-rays are produced as little as possible, the scattered X-rays decrease energy as described above, and thus the raw data RE1 in the energy region E1 hardly includes scattered X-ray photons. The attenuation coefficient map ME1 is thereby considered to be hardly affected by the scattered radiation. Besides, if scattered radiation is quantitatively corrected by the Triple Energy Window method, etc., the scattered radiation can be made further less influential The attenuation coefficient map transforming unit 64 shown in FIG. 4 has a function to transform the attenuation coefficient map ME1 in the energy region E1 into an attenuation coefficient map ME2 in the energy region E2.

Figure 9:
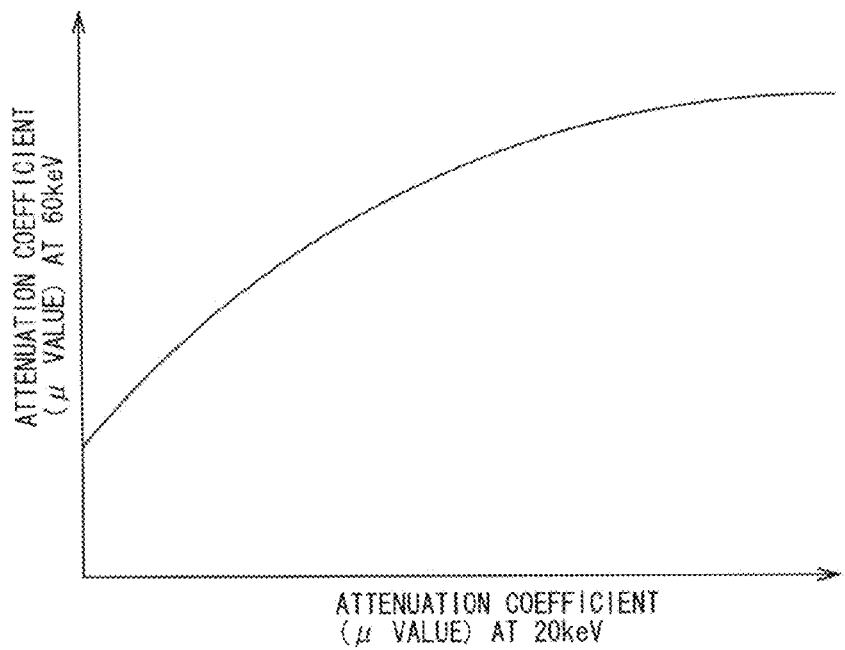
FIG. 9 is a diagram illustrating a transforming equation for producing an attenuation coefficient map after energy transformation.

FIG. 9 is a diagram illustrating a transforming equation for producing the attenuation coefficient map ME2 after energy transformation.

FIG. 9 illustrates a transforming equation for transforming a p value in the attenuation coefficient map ME1 at 60 keV being the energy region E1 produced by the attenuation coefficient map producing unit 63 into a p value, e.g., at 20 keV in the energy region E2 excepting 60 keV. The attenuation coefficient map transforming unit 64 produces the attenuation coefficient map ME2 in the energy region E2 excepting 60 keV on the basis of the attenuation coefficient map ME1 at 60 keV being the energy region E1 produced by the attenuation coefficient map producing unit 63. A transformation table based on the transforming equation is prepared for energy transformation, and the attenuation coefficient map ME1 is transformed into the attenuation coefficient map ME2 according to the transformation table.

The simulation performing unit 65 shown in FIG. 4 has a function to perform a simulation of scattered radiation by using the attenuation coefficient map ME2 after the transformation done by the attenuation coefficient map transforming unit 64, and to produce a distribution DE2 of scattered X-ray photons having reached the detector 23 (scattered photon distribution). If a plurality of attenuation coefficient maps ME2 exists for a plurality of energy regions E2, the simulation performing unit 65 performs a simulation for each of the attenuation coefficient maps ME2.

Then, the simulation of scattered radiation performed by the simulation performing unit 65 will be explained by the use of a flowchart shown in FIG. 10.

A probability that Compton scattering occurs is represented by a ratio of the number of scattered photons to the number of incident photons over a total cross section per one electron (o), which is indicated by the Klein-Nishina formula (I). That is, regarding probability that the number of incident photons is scattered into an infinitesimal solid angle d$\Omega$ in a scattering angle direction $\theta$, a differential cross section per one free electron (d$\sigma$/d$\Omega$) is calculated according to the equation (1) shown below.

Suppose that the X-ray tube 21 emits one X-ray photon at first (step ST1). Let the X-ray photon move ahead by a unit distance (step ST2), and decide whether the X-ray photon reaches out of a calculation range (step ST3). If the step ST3 branches off to YES, i.e., it is decided that the X-ray photon moves ahead by a unit distance at the step ST2 and resultantly the X-ray photon has not reached the calculation range, it is decided whether the X-ray photon reaches a detection face of the detector 23 (step ST4). If the step ST4 branches off to NO, i.e., it is decided that the X-ray photon moves ahead by a unit distance at the step ST2 and resultantly the X-ray photon has not reached the detection face of the detector 23, a scattering probability and a scattering angle at that time are calculated according to the equation (1) shown below (step ST5). Then, return to the step ST2 for letting the X-ray photon move ahead by another unit distance so as to repeat the process.

$$\frac{d\sigma}{d\Omega} = Zr_0^2 \left[\frac{1}{1+\alpha(1-\cos\theta)}\right]^2 \left[\frac{1+\cos^2\theta}{2}\right] \quad (1)$$

$$\left[1 + \frac{\alpha^2(1-\cos\theta)^2}{(1+\cos^2\theta)[1+\alpha(1-\cos\theta)]}\right]$$

$\frac{d\sigma}{d\Omega}$: differential scattering cross section $$\alpha \cong \frac{h\nu}{m_0 c^2}$$

$r_0$: classical electron radius $m_0$: atomic mass

Meanwhile, if the step ST3 branches off to NO, i.e., it is decided that the X-ray photon moves ahead by a unit distance at the step ST2 and resultantly the X-ray photon has reached out of the calculation range, it is decided whether to end the calculation (step ST8). If the step ST8 branches off to NO, i.e., it is decided not to end the calculation, return to the step ST1 for another single X-ray photon.

If the step ST4 branches off to YES, i.e., it is decided that the X-ray photon moves ahead by a unit distance at the step ST2 and resultantly the X-ray photon has met the detection face of the detector 23, it is decided whether the X-ray photon is detected by the detector 23 according to energy of the X-ray photon and detection probability of the detector 23 (step ST6). If the step ST6 branches off to YES, i.e., it is decided that the X-ray photon is detected by the detector 23, reflect detected information upon the scattered photon distribution DE2 (step ST7). Meanwhile, if the step ST6 branches off to NO, i.e., it is decided that the X-ray photon is not detected by the detector 23, it is decided whether to end the calculation (step ST8).

If the step ST8 branches off to YES, i.e., it is decided that the calculation ends, the operation ends.

Figure 10:
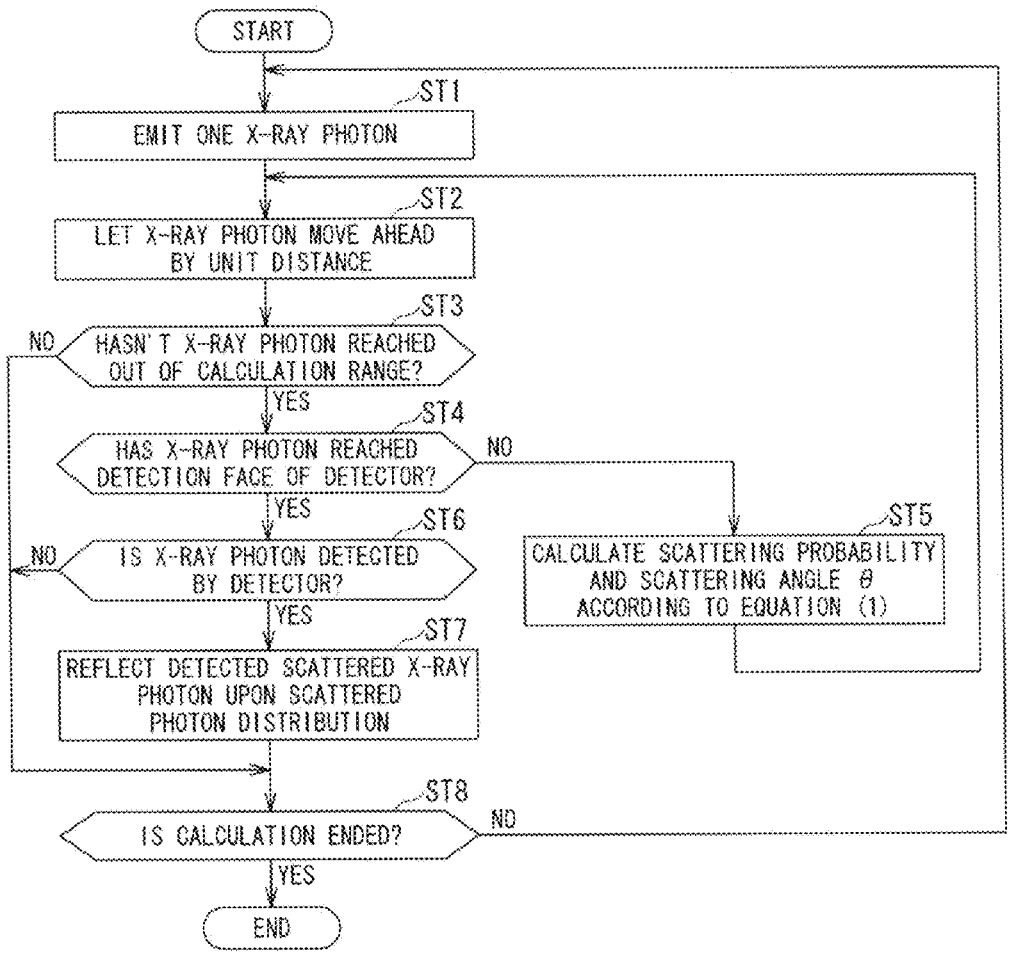
FIG. 10 is a diagram showing a flowchart of a simulation of scattered radiation.

According to the flowchart shown in FIG. 10, if a calculation is performed for a certain X-ray photon in an energy region Ek and the energy of the X-ray photon is in the range of the energy region E1 as a result of the calculation performed at the step ST5, the process returns to the step ST2 and is repeated. The embodiment is not limited to that flow, though. If a calculation is performed for a certain X-ray photon in an energy region Ek and the energy of the X-ray photon is in the range of the energy region E1 as a result of the calculation performed at the step ST5, the calculation may end for the relevant X-ray photon and the process may return to the step ST1 for another single X-ray photon, or the information on the relevant X-ray photon may be held and used for calculation in the energy region E1. Incidentally, the latter contributes to enhancing a quantitative feature of the scattered ray correction but at the cost of a longer time for calculation.

Figure 11:
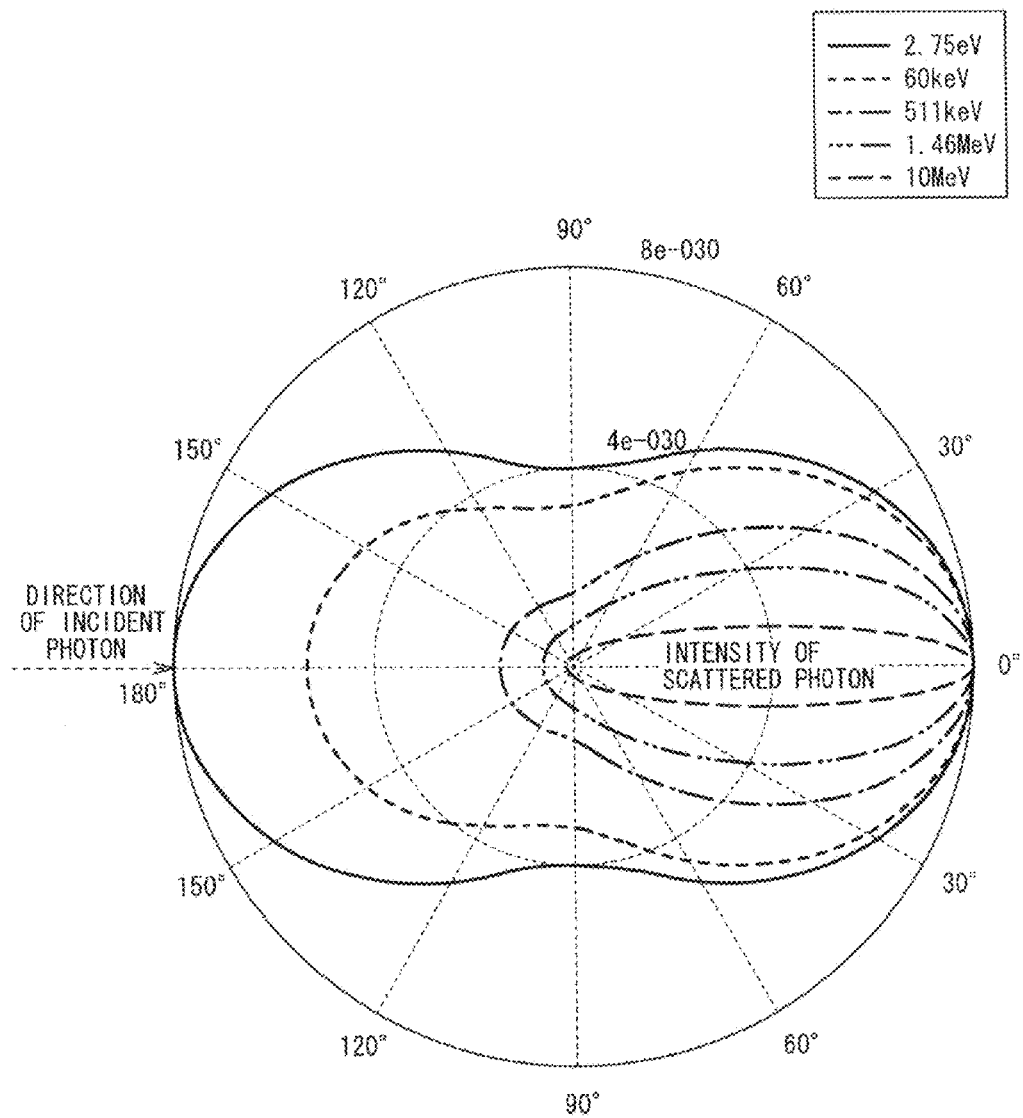
FIG. 11 is a diagram showing a scattering angle and its probability calculated by an equation (1).

FIG. 11 is a diagram showing a scattering angle and its probability calculated by the equation (1).

As shown in FIG. 11, the scattered photon distribution DE2 is nearly symmetrical with respect to 90 degrees when energy of the incident photon is very low, and scattering towards the front increases as the energy of the photon increases. If the above equation (1) is integrated over the total solid angle regarding the scattering angle θ, the total cross section (total scattering coefficient) σ per one electron is obtained.

Incidentally, the simulation performing unit 65 can reduce an amount of calculation by setting a threshold to the energy of the X-ray photon in the simulation of scattered radiation at the step ST3 described above. Further, the simulation performing unit 65 can reduce an amount of calculation as well by limiting the number of times of scattering of the X-ray photon in the simulation of scattered radiation at the step ST3 described above. Further, the simulation performing unit 65 can reduce an amount of calculation as well by limiting the calculation range in the simulation of scattered radiation at the step ST3 described above.

Return to explanation in FIG. 4. The correction processing unit 66 has a function to correct the raw data RE2 in the energy region E2 distinguished by the energy distinguishing unit 62 on the basis of the scattered photon distribution DE2 produced by the simulation performing unit 65 so as to produce raw data after correction R'E2. The correction processing unit 66 subtracts the scattered photon distribution DE2 from the raw data RE2 so as to produce the raw data after correction R'E2. If a plurality of scattered photon distributions DE2 exists for a plurality of energy regions E2, the correction processing unit 66 corrects a plurality of raw data RE2 in each of the energy regions E2 on the basis of the plural scattered photon distributions DE2.

The image reconstructing unit 67 has a function to reconstruct a reconstructed image on the basis of the raw data after correction R'E2 by means of the correction processing unit 66 so as to produce a reconstructed image IE. The reconstructed image IE produced by the image reconstructing unit 67 is stored in the image memory 43 and is displayed via the display device 46.

As the photon counting type X-ray CT apparatus 1 according to the embodiment can quantitatively correct scattered radiation by producing an X-ray photon whose highest energy is higher than the highest peak energy of the characteristic X-rays, an exact and precise CT image can be provided.

Further, as the photon counting type X-ray CT apparatus 1 according to the embodiment can more quantitatively correct scattered radiation by producing an X-ray photon whose highest energy is higher than and around the highest peak energy of the characteristic X-rays, an exact and precise CT image can be provided.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A photon counting type X-ray computed tomography apparatus comprising:
    an X-ray tube configured to produce an X-ray photon whose highest energy is higher than highest peak energy of characteristic X-rays;
    an X-ray detecting material configured to detect the X-ray photon;
    an attenuation coefficient map producing unit configured to produce a first attenuation coefficient map which corresponds to a first energy region including the highest peak energy of the characteristic X-rays;
    an attenuation coefficient map transforming unit configured to transform the first attenuation coefficient map into a second attenuation coefficient map of a second energy region which is different from the first energy region;

a simulation performing unit configured to perform a simulation of scattered radiation on the basis of the second attenuation coefficient map so as to produce a scattered photon distribution of scattered X-ray photons; and an image reconstructing unit configured to produce data before reconstruction on the basis of the detected X-ray photon which corresponds to the second energy region, to correct and process the data before reconstruction with the scattered photon distribution so as to produce corrected data, and to reconstruct an image corresponding to the second energy region for which scattered radiation is corrected.

2. The photon counting type X-ray computed tomography apparatus according to claim 1, wherein the simulation performing unit produces the scattered photon distribution by making a plurality of X-ray photons emitted by the X-ray tube move ahead by a unit distance for calculating a scattering probability and a scattering angle and by carrying out a process for making the plural X-ray photons move ahead by a unit distance until, as a result of the calculation, the plural X-ray photons reach out of a calculation range.

3. The photon counting type X-ray computed tomography apparatus according to claim 2, wherein the simulation performing unit sets a threshold to energy of the X-ray photons in the simulation of scattered radiation.

4. The photon counting type X-ray computed tomography apparatus according to claim 2, wherein the simulation performing unit limits the number of times of scattering of the X-ray photons in the simulation of scattered radiation.

5. The photon counting type X-ray computed tomography apparatus according to claim 2, wherein the simulation performing unit limits a calculation range in the simulation of scattered radiation.

6. The photon counting type X-ray computed tomography apparatus according to claim 1, wherein the X-ray tube produces an X-ray photon in such a way that the highest energy is around the highest peak energy of the characteristic X-rays.

7. A method for correcting scattered radiation comprising:

producing an X-ray photon whose highest energy is higher than highest peak energy of characteristic X-rays from an X-ray tube;

detecting the X-ray photon by means of an X-ray detecting material;

producing a first attenuation coefficient map which corresponds to a first energy region including the highest peak energy of the characteristic X-rays;

transforming the first attenuation coefficient map into a second attenuation coefficient map of a second energy region which is different from the first energy region;

performing a simulation of scattered radiation on the basis of the second attenuation coefficient map so as to produce a scattered photon distribution of scattered X-ray photons; and producing data before reconstruction on the basis of the detected X-ray photon which corresponds to the second energy region, correcting and processing the data before reconstruction with the scattered photon distribution so as to produce corrected data, and reconstructing an image corresponding to the second energy region for which scattered radiation is corrected.

8. The method for correcting scattered radiation according to claim 7 further comprising, for producing the scattered photon distribution:

making a plurality of X-ray photons emitted by the X-ray tube move ahead by a unit distance for calculating a scattering probability and a scattering angle; and carrying out a process for making the plural X-ray photons move ahead by a unit distance until, as a result of the calculation, the plural X-ray photons reach out of a calculation range.

9. The method for correcting scattered radiation according to claim 8, wherein a threshold is set to energy of the X-ray photons in the simulation of scattered radiation.

10. The method for correcting scattered radiation according to claim 8, wherein the number of times of scattering of the X-ray photons is limited in the simulation of scattered radiation.

11. The method for correcting scattered radiation according to claim 8, wherein a calculation range is limited in the simulation of scattered radiation.

12. The method for correcting scattered radiation according to claim 7, wherein the X-ray tube produces an X-ray photon in such a way that the highest energy is around the highest peak energy of the characteristic X-rays.

* * * * *